United States Patent [19]

Beshty et al.

[11] Patent Number: 5,231,187

[45] Date of Patent: Jul. 27, 1993

[54] SYNTHESIS OF 4-METHYL THIAZOLE

[75] Inventors: Bahjat S. Beshty, Lower Makefield, Pa.; Frank P. Gortsema, Pleasantville, N.Y.; George T. Wildman, Westfield; John J. Sharkey, No. Brunswick, both of N.J.

[73] Assignee: Merck & Co., Inc., Rahway, N.J.

[21] Appl. No.: 767,030

[22] Filed: Oct. 1, 1991

Related U.S. Application Data

[63] Continuation-in-part of Ser. No. 597,639, Oct. 15, 1990, abandoned.

[51] Int. Cl.$^5$ ............................................. C07D 277/20
[52] U.S. Cl. .................................................... 548/202
[58] Field of Search ......................................... 548/202

[56] References Cited

U.S. PATENT DOCUMENTS

| | | | |
|---|---|---|---|
| 3,308,069 | 5/1967 | Wadlinger et al. | 548/202 |
| 3,702,886 | 11/1972 | Argosor et al. | 548/202 |
| 4,247,388 | 1/1981 | Banta et al. | 548/202 |
| 4,282,364 | 8/1981 | Amato | 548/202 |
| 4,284,784 | 8/1981 | Ho | 548/202 |
| 4,312,790 | 1/1982 | Butter et al. | 548/202 |
| 4,469,908 | 9/1984 | Burress | 548/202 |

FOREIGN PATENT DOCUMENTS 370553   5/1990   European Pat. Off. .
2544341 10/1975   Fed. Rep. of Germany .

OTHER PUBLICATIONS

Chem. Abs. (1985), 102, No. 4, pp. 207, 28107P.
Science (1990), 248, pp. 1190–1191, by J. Alper.

*Primary Examiner*—Robert Gerstl
*Attorney, Agent, or Firm*—Sylvia A. Ayler; Mark R. Daniel; Joseph F. DiPrima

[57] ABSTRACT

Isopropylidene methylamine is reacted with $SO_2$ to form 4-methyl thiazole in the presence of a modified zeolite catalyst that has been ion-exchanged with an ammonium salt and porefilled with an alkali metal salt.

10 Claims, No Drawings

SYNTHESIS OF 4-METHYL THIAZOLE

PRIOR APPLICATION INFORMATION

This application is a continuation-in-part of prior application Ser. No. 07/597,639, filed Oct. 15, 1990, now abandoned.

BACKGROUND OF THE INVENTION

Thiabendazole, 2-(4-thiazolyl)-1H-benzimidazole, is a systemic fungicide used for spoilage control of citrus fruit, for treatment and prevention of Dutch elm disease in trees, and for control of fungal diseases of seed potatoes.

One route for the synthesis of thiabendazole employs 4-methyl thiazole (4-MT) as an intermediate. Known methods for the synthesis of this compound used hazardous chemicals, or gave yields that were too low, or for other reasons were uneconomic.

OBJECTS OF THE INVENTION

It is, accordingly, an object of the present invention to provide an improved process for the synthesis of 4-methyl thiazole. Another object is to provide a process that does not involve the use of hazardous chemicals. A further object is to provide a process that gives improved yields of 4-methyl thiazole. Still another object is to provide a modified zeolite catalyst that promotes the synthesis of 4-methyl thiazole. These and other objects of the present invention will be apparent from the present application.

SUMMARY OF THE INVENTION

Zeolite catalysts having a Constraint Index of 1 to 12, when ion-exchanged with an ammonium salt and pore-filled with an alkali metal salt, preferably a cesium salt, are a particularly effective catalyst for reacting isopropylidene methylamine (Imine) with $SO_2$ to form 4-MT in one step.

DETAILED DESCRIPTION

The present invention relates to a novel catalyst used in the synthesis of 4-methyl thiazole, an intermediate used in the synthesis of thiabendazole. More particularly, it relates to the synthesis of 4-MT using a modified zeolite catalyst.

According to the present invention, isopropylidene methylamine (imine) of the formula $(CH_3)_2C=NCH_3$ is reacted with sulfur dioxide, $SO_2$, over a modified zeolite catalyst in the presence of nitrogen, $N_2$, to form 4-MT of the formula

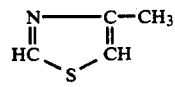

The starting imine is known per se and may be prepared by any suitable method. One method, by way of example, is to react acetone with methyl amine.

The starting material for the catalyst of the present invention is crystalline zeolite having unusually low alumina contents, i.e., high silica to alumina ratios, even ratios exceeding 30. An important characteristic of this class of zeolites is that it provides constrained access to and egress from the intracrystalline free space by virtue of having an effective pore size intermediate between the small pore Linde A and the large pore Linde X, i.e., the pore windows of the structure have about a size such as would be provided by 10-membered rings of silicon and aluminum atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. The preferred type of zeolite has a silica to alumina mole ratio of at least 12, preferably at least about 30, and a structure providing constrained access to the intracrystalline free space. The silica to alumina ratio may be determined by conventional analysis. This ratio is meant to represent, as closely as possible, the ratio in the rigid anionic framework of the zeolite crystal and to exclude alumina in the binder or other form within the channels. Such zeolites acquire, after activation, an intracrystalline sorption capacity for normal hexane (n-hexane) which is greater than that for water, i.e., they exhibit hydrophobic properties. In addition to having an effective pore size so as to freely sorb n-hexane, the zeolite must provide constrained access to larger molecules.

Rather than attempt to judge from crystal structure whether or not a particular zeolite possesses the necessary constrained access to molecules larger than normal paraffins, a simple determination of the "Constraint Index" (CI) may be made by passing continuously, a mixture of an equal weight of n-hexane and 3-methyl pentane over a small sample, approximately one gram or less, of the zeolite at atmospheric pressure according to the following procedure. A sample of the zeolite, in the form of pellets or extrudate, is crushed to a particle size about that of coarse sand, and mounted in a glass tube and treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream a sample of the effluent is taken and analyzed, most conveniently by gas chromatography, to determine the fraction remaining unchanged for each of the two hydrocarbons. The $$CI = \frac{\log 10 \text{ (fraction on n-hexane remaining)}}{\log 10 \text{ (fraction of 3-methylpentane remaining)}}$$

The CI approximates the ratio of the cracking rate constants for the two hydrocarbons. Zeolites suitable for use as starting materials in the present invention are those having a CI of 1 to 12. These starting materials are described in more detail in U.S. Pat. No. 4,469,908.

The catalyst used in the method of the present invention is a zeolite modified by treatment with an alkali metal salt. The alkali metal can be, for instance, K, Rb, or Cs. The preferred alkali metal is Cs. The anion with which the alkali metal is associated can be, for example, $SO_4^=$, $CO_3^=$, acetate, $NO_3^-$, and $HCO_3^-$. the preferred anion is $SO_4^=$.

According to the present invention, the zeolite is treated initially, on a weight basis, with a solution of from about 5 to about 20 parts by weight of $NH_4NO_3$. Preferably, the zeolite is subjected to several treatments using each time on a weight basis from about 2 to about 7 parts of NH$_4$NO$_3$ per treatment, with washing the zeolite after each treatment. This treatment is generally carried out at room temperature although elevated temperatures can be employed. Alternatively, this reduction or hydrogenation of the zeolite can be accomplished using a mineral acid such as hydrochloric, nitric, sulphuric or phosphoric acid, with hydrochloric acid being preferred. Preferred molar ranges include 0.1 to 3M, with most preferred being 0.1 to 0.5M.

Following the NH$_4$NO$_3$ treatment, the zeolite is ion-exchanged and porefilled with a quantity of the alkali metal salt effective to give an alkali metal content in the zeolite that is greater than the amount of alkali metal needed to provide a fully cation-exchanged zeolite. In general this amount is from about 10% to about 40% by weight of the weight of the zeolite. The alkali metal porefilled zeolite is then dried and calcined. The drying conditions are not critical.

Drying may be carried out under vacuum, at atmospheric pressure or above. The drying temperature usually will depend upon the solvent used in the impregnation step. For solvents that are liquid below room temperature, the drying temperature can be below room temperature. For solvents that are liquid at or above room temperature, higher temperatures up to about 200° C. can be used.

After drying the porefilled zeolite is calcined at elevated temperatures of from about 150° C. to about 825° C., preferably from about 175° C. to about 550°. Within the foregoing temperature ranges, different temperature stages can be employed, for example, in a three hour calcining cycle, the impregnated zeolite can be heated for one about hour at about 200° C. and for about two hours at about 500° C. Calcining times depend upon the calcining conditions selected and typically are in the range of from about one hour to about 10 hours. Any calcining conditions can be used as long as they do not substantially destroy zeolite crystallinity.

If desired, the drying and calcining steps can be combined.

The following examples illustrate the present invention without, however, limiting the same thereto.

EXAMPLE 1

A: Preparation of Cs$_2$SO$_4$ Pore-filled ZSM-5 Zeolite Catalyst

A ZSM-5 zeolite powder, 20.1 g, having a Constraint Index (CI) within the range of 1–12, was stirred with 1 liter of 1M NH$_4$NO$_3$ for 1 hour at room temperature and then filtered. An additional liter of fresh NH$_4$NO$_3$ was added and the foregoing procedure was repeated. Then an additional liter of fresh NH$_4$NO$_3$ was added and the foregoing procedure was repeated once again. The zeolite filter cake was washed with 4×250 ml deionized water, resuspending the filter cake after each wash. The filter cake was then placed in an air or N$_2$ purged oven and dried at a temperature of up to 110° C. until a constant weight was obtained.

The NH$_4$NO$_3$ treated ZSM-5 powder was porefilled with a concentrated aqueous Cs$_2$SO$_4$ solution in the following manner. The water pore volume of the zeolite powder was measured by standard absorption techniques, and was found to be typically 1.2 ml/g. The quantity of cesium sulfate required to give a 25 weight % Cs content in the zeolite, 9.11 g, was dissolved in enough deionized water to give 24 ml of solution which was added to the zeolite powder with stirring. The paste that formed initially was stiff and difficult to mix, but with continued stirring formed a uniform thick slurry. The paste was dried at room temperature in air for about two hours until it formed a rigid solid, then dried for 6–10 hours or overnight in an oven at 50°–70° with an air or N$_2$ purge. The solid material was calcined in air using the following schedule:

1) heat from ambient to 200° C. at a rate of 20° C./minute
2) hold for 1 hour at 200° C.
3) heat to 500° C. at a rate of 20° C./minute
4) hold for 2 hours at 500° C.
5) cool to ambient temperature.

A total of 28.8 g of calcined Cs$_2$SO$_4$-loaded ZSM-5 zeolite was obtained. This material was sized using US standard screens to give a −16+30 mesh fraction for microreactor testing. Chemical analysis of the product showed the presence of 24.1% Cs by atomic absorption measurements. BET single point surface area measurement gave 190 square meters/g (m$^2$/g).

B. Preparation of Isopropylidene Methylamine (Imine)

Imine was prepared according to the reaction:

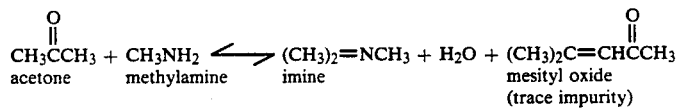

In the final equilibrium mixture, acetone was determined by gas chromatography (GC) from acetone standards, water by Karl Fischer titration, mesityl oxide from GC standards, and imine by differential mass balance.

C. Preparation Of 4-Methyl Thiazole (4-MT)

Catalytic performance was evaluated by measuring the conversion, selectivity, and lifetime in the reaction:

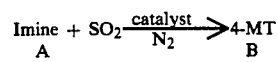

A 2 g charge of catalyst was placed in a tubular stainless steel reactor between quartz wool plugs and tested by running the foregoing reaction under the following conditions:

N$_2$ feed rate: 150 cc/minute
Feedstock rate flow: 0.033 cc/minute of imine
SO$_2$ flow rate: 10 cc/minute
Reactor wall temperature: 470° C.
Pressure: approximately atmospheric.

The reaction was run continuously for a total of 175 hours when it was intentionally terminated. The catalyst showed an overall conversion of 86% and a selectivity to 4-MT of 62%, based on the gas phase "imine" content. For catalyst performance evaluation, lifetime was defined as the time, in hours, required for the yield of "4-MT" to decline to 30 weight %. The other variables were defined as follows, based on the foregoing equation:

$$\text{conversion} = \frac{A_{in} - A_{out}}{A_{in}}$$

$$\text{selectivity} = \frac{B}{A_{in} - A_{out}}$$

$$\text{yield} = \frac{B}{A_{in}}$$

where
A = imine concentration and
B = 4-MT concentration.

EXAMPLE 2

Preparation of a $Cs_2SO_4$ Porefilled, Silica Bonded ZSM-5 Zeolite Extrudate, Activated After Ammonium Exchange A silica bonded ZSM-5 zeolite, 74 g, having a CI within the range of 1-12, was ion exchanged three times with 2 liters of 1M $NH_4NO_3$ at room temperature. After the third exchange the excess solvent was decanted and the extrudate was washed with distilled water (5 ml/g extrudate) two times at room temperature with agitation. The excess water was decanted and the extrudate dried in an oven to a final temperature of 100° C. and the extrudate had reached a constant weight. The extrudate was calcined to 500° C. to drive off $NH_3$ using the same heating schedule as example 1.

The activated form of the extrudate was porefilled with a $Cs_2SO_4$ solution to give a 25 weight % Cs content based on the total extrudate weight. The extrudate was air dried at room temperature, followed by heating in an oven to 100° C. Calcination was carried out by heating the dried extrudate to 500° C. in air using the same heating schedule described in Example 1.

The calcined material, when tested under the same conditions described in Example 1, exhibited a lifetime of 15 hours, selectivity to 4-MT of 41% and conversion of 82%.

EXAMPLE 3

Preparation of a $Cs_2SO_4$ Porefilled $NH_4NO_3$ Ion Exchanged ZSM-5 Extrudate, Not Activated After $NH_4+$ Exchange A commercially obtained ZSM-5 1/16" extrudate sample (75 g), having a CI in the range of 1-12, containing 20% silica binder identical to that described in Example 2, was ion exchanged with 2 L of 1M $NH_4NO_3$ solution at a temperature of 75°-85° C. for 1 hour. The liquid was decanted and fresh solution added. The ion exchange process was repeated a total of 3 times. After the last exchange, the extrudates were washed with 300 ml of distilled water for ½ hour. The washing procedure was repeated for a total of 4 times. After the final wash, the exchanged extrudates were dried for 12 hours at 120° C. to constant weight.

The extrudates were porefilled with a cesium sulfate solution using a value of 0.66 ml $H_2O$/g zeolite as the measured pore volume. A cesium sulfate solution was prepared by dissolving 34.49 g $Cs_2SO_4$ in enough deionized water to give approximately 50 ml of solution. The solution was added to the extrudates in a 500 ml round bottom flask. The flask was then attached to a rotary evaporator to tumble the extrudates to give a uniform cesium loading throughout the pellets. After approximately 4 hours of tumbling, an air stream was directed on the pellets and they were dried by tumbling for another 8 hour period.

The extrudates were calcined to 500° C. in air using the procedure described in Example 1. A performance test of this catalyst material using a 2 g sample and the apparatus and procedure described in Example 1 gave a lifetime of 15 hours, selectivity to 4-MT of 46% and conversion of 87%.

EXAMPLE 4

Preparation of a cesium sulfate porefilled silicalite powder having a $SO_2/Al_2O_3$ ratio of 240

A sample of silicalite, a commercial molecular sieve designated S-115 having the ZSM-5 structure, having a CI in the range of 1-12, was obtained from Union Carbide Corporation. A 50 g sample of powder was porefilled with a cesium sulfate solution prepared by dissolving 17.1 g in enough distilled water to yield 20 ml of solution. The pH of the solution was adjusted to 3.86 by addition of sulfuric acid. The solution was added to the powder, stirred to make a homogeneous paste and dried over a period of 14 hours at 50° C. The material was calcined according to the schedule in Example 1. Analyses of the cesium content by atomic absorption spectroscopy gave 19.2% Cs. BET surface area measurement gave a value of 288 $m^2$/g.

The calcined material, tested under the conditions described in Example 1, showed a lifetime of 2.9 hours, a selectivity to 4-MT of 38 wt % and conversion of 64 wt %.

EXAMPLE 5

Preparation of a cesium sulfate porefilled ammonium nitrate ion exchanged beta zeolite, not activated after the ammonium exchange A commercially obtained beta zeolite powder C-815 from PQ Corporation, 20.6 g, having a CI in the range of 1-12 and a $SiO_2/Al_2O_3$ ratio of 25, was ion exchanged with 1 liter of 1M ammonium nitrate for 1 hour. The liquid was separated from the solid by pressure filtration and the filter cake was resuspended in 1 l of fresh ammonium nitrate. A total of three ammonium nitrate exchanges were carried out. After the last exchange the zeolite was washed three times with 500 ml portions of distilled water, resuspending the filter cake between each wash. The resulting filter cake, 18.7 g, was dried for 14 hours at temperatures up to 100° C.

The water pore volume of the zeolite was determined to be 1.5 ml/g. A cesium sulfate solution was prepared by dissolving 8.53 g in enough water to give 28 ml solution. The solution was added to the powder and thoroughly mixed to give a uniform paste. This material was air dried for 5 hours, followed by oven drying at temperatures up to 120° C. for a period of 12 hours. The powder was calcined to 500° C. using the heating schedule described in Example 1. The sample was tested for catalytic performance using a 2 g quantity and the apparatus and procedure described in Example 1. The catalyst lifetime was approximately 50 hours.

The selectivity initially was low but increased over time.

EXAMPLE 6

A ZSM-5 zeolite powder having a constraint index (CI) of 8.3, 75.3 g, was stirred with 2 liters of 1M $NH_4NO_3$ for 1 hour at room temperature and then filtered. An additional 2 liters of fresh $NH_4NO_3$ solution was added and the foregoing $NH_4+$ ion exchange procedure was repeated. This procedure was repeated a total of three times. After the final $NH_4^+$ exchange, the filter cake was washed three times with 700 ml portions of deionized water, resuspending the filter cake after each wash. The filter cake was allowed to stand at room temperature for two hours, then heated in an oven at temperatures from 50° C. to 135° C. until constant weight was obtained.

The $NH_4NO_3$ treated ZSM-5 powder was porefilled with a concentrated $Cs_2SO_4$ solution in the following manner.

The water pore volume of the zeolite powder was measured and found to be 0.81 ml water/g zeolite by standard adsorption techniques. The quantity of $Cs_2SO_4$ required to give 25 weight % Cs content in the recovered $NH_4NO_3$ ion exchanged zeolite, 71.67 g, was determined to be 32.5 g. This amount of the salt was weighed out and added to enough deionized water to give 58 ml solution. The stirred solution was added to the $NH_4^+$ ion exchanged powder and stirred to give a thick paste. The paste was dried at room temperature for four hours, followed by heating in an oven at 75° C. until constant weight was obtained.

The dried cesium sulfate ammonium exchanged ZSM-5 material was formed into silica bonded extrudates using Ludox AS-40 as the source of the silica. The silica content was 20% (17.92 g as $SiO_2$) based on the weight of the ammonium exchanged zeolite (71.67 g). The silica content of the AS-40 Ludox was determined to be 41%. Therefore, 43.7 g Ludox was weighted out and gelled by adding dropwise, a saturated solution of ammonium acetate. The gelled Ludox was added to the cesium sulfate impregnated ammonium nitrate ion exchanged ZSM-5 powder and mixed to give a uniform mixture. Enough distilled water was added to this solid by spraying to give approximately a 40% water content. This material was extruded into 1/16" pellets using a Bonnot extruder. The extrudates were dried at room temperature for five hours, heated at 130° C. until constant weight was obtained and then calcined to 500° C. using the following heating schedule:

1. ambient to 200° C. at a rate of 20° C./minute;
2. hold for one hour at 200° C.;
3. 200° C. to 500° C. at a rate of 20° C./minute;
4. hold for two hours at 500° C.;
5. cool to ambient temperature.

A total of 103 gms of calcined extrudates were obtained. These were crushed to give approximately 1/16"×1/16" size for testing in a pilot scale reactor. A 8 gm sample size was used and evaluated at the following test conditions.

| | |
|---|---|
| Imine feed rate: | 0.28 cc/min |
| $N_2$ flow: | 1.2 liters/min |
| feedstock composition: | 2:1 acetone:imine |
| $SO_2$ flow rate: | 80 cc/min |
| Reactor wall temperature: | 467° C. |
| Pressure: | approximately atmospheric |

The reaction was run continuously for a total of 87 hours. The catalyst showed an overall conversion of the feedstock of 77% and a selectivity to 4-MT of 73 weight %, for an overall yield of 47 weight %, based on the gas phase "imine" content.

What is claimed is:

1. A method for catalytically converting isopropylidene methylamine and sulfur dioxide to 4-methyl thiazole comprising passing isopropylidene methylamine and sulfur dioxide over a zeolite powder having a Constraint Index of from about 1 to about 12 that has been ion-exchanged with either an ammonium salt or a mineral acid and additionally with an alkali metal salt before being porefilled with an alkali metal salt.

2. A method according to claim 1 wherein the ammonium salt is a chloride, bromide, nitrate or sulfate.

3. A method according to claim 2 wherein the ammonium salt is a nitrate.

4. A method according to claim 1 wherein the alkali metal salt is an acetate, bicarbonate, carbonate, nitrate or sulfate.

5. A method according to claim 4 wherein the salt is a sulfate.

6. A method according to claim 1 wherein the alkali metal of the salt is K, Rb or Cs.

7. A method according to claim 6 wherein the alkali metal is Cs.

8. A method according to claim 5 wherein the salt is $Cs_2SO_4$.

9. A method as claimed in claim 1, wherein said zeolite powder has been formed into an extrudate after being porefilled with an alkali metal salt.

10. A method according to claim 1 wherein the zeolite is heat treated after being ion-exchanged.

* * * * *